US010799720B2

(12) United States Patent
Vilsmeier (10) Patent No.: US 10,799,720 B2
(45) Date of Patent: *Oct. 13, 2020

(54) DETERMINING AN IRRADIATION REGION FOR RADIOTHERAPY BASED ON MODEL PATIENT DATA AND PATIENT IMAGE DATA

(71) Applicant: Brainlab AG, Munich (DE)

(72) Inventor: Stefan Vilsmeier, Munich (DE)

(73) Assignee: BRAINLAB AG, Munich (DE)

( * ) Notice: Subject to any disclaimer, the term of this patent is extended or adjusted under 35 U.S.C. 154(b) by 147 days.

This patent is subject to a terminal disclaimer.

(21) Appl. No.: 16/149,410

(22) Filed: Oct. 2, 2018

(65) Prior Publication Data
US 2019/0038920 A1 Feb. 7, 2019

Related U.S. Application Data

(63) Continuation of application No. 14/438,487, filed as application No. PCT/EP2012/071245 on Oct. 26, 2012, now Pat. No. 10,137,315.

(51) Int. Cl.
*A61N 5/10* (2006.01)

(52) U.S. Cl.
CPC ........... *A61N 5/1049* (2013.01); *A61N 5/103* (2013.01); *A61N 2005/1041* (2013.01); *A61N 2005/1055* (2013.01)

(58) Field of Classification Search
CPC .................. A61N 5/1049; A61N 5/103; A61N 2005/1055; A61N 2005/1041; A61N 5/1048; A61B 2090/364; A61B 6/469; G06T 2207/20128; G06T 7/187
See application file for complete search history.

(56) References Cited

U.S. PATENT DOCUMENTS

| 2004/0120452 | A1 | 6/2004 | Shapiro |
| 2004/0202610 | A1 | 10/2004 | Adair |
| 2006/0293583 | A1 | 12/2006 | Saracen et al. |
| 2007/0019846 | A1 | 1/2007 | Bullitt et al. |
| 2007/0189591 | A1 | 8/2007 | Lu et al. |
| 2010/0232572 | A1 | 9/2010 | Nord et al. |

FOREIGN PATENT DOCUMENTS

WO 2012085722 A1 6/2012

OTHER PUBLICATIONS

European Patent Office, International Search Report and Written Opinion for corresponding PCT/EP2012/071245; dated May 21, 2013, pp. 8.
Lahorte, P., Office Action, pp. 1-4, European Patent Office, Application No. EP12787400.6 dated Aug. 29, 2017.

*Primary Examiner* — Kaylee R Wilson
(74) *Attorney, Agent, or Firm* — Tucker Ellis LLP (57) ABSTRACT

The invention relates to a method of determining a radiotherapy treatment plan for radiotherapy treatment of a treatment body part of a patient's body. The method can include acquiring treatment target position data comprising treatment target position information describing the position of a treatment target to be treated by radiotherapy in the treatment body part. Statistic model target region position data is acquired, which describes the position of a model target region in a model body part corresponding to the treatment body part. Based on the treatment target data and the statistic model target region position data, irradiation region position data is determined that describes the position of an irradiation region to be treated by irradiation with treatment radiation in the treatment body part.

12 Claims, 3 Drawing Sheets

DETERMINING AN IRRADIATION REGION FOR RADIOTHERAPY BASED ON MODEL PATIENT DATA AND PATIENT IMAGE DATA

RELATED APPLICATION DATA

This application is a continuation of U.S. patent application Ser. No. 14/438,487, filed on Apr. 24, 2015. Application Ser. No. 14/438,487 is a national phase application of International Application No. PCT/EP2012/071245 filed Oct. 26, 2012 and published in the English language. The entireties of the aforementioned applications are herein incorporated by reference.

TECHNICAL FIELD

The invention is directed to a method, in particular a data processing method, of determining a radiotherapy treatment plan in accordance with claim 1. The invention is also directed to a computer program corresponding to the method and a computer running that computer program as well as a radiotherapy system including that computer.

BACKGROUND

In radiotherapy, a user such as radiologist or medical technician presently determines a treatment plan based on the merits of each individual medical case for a specific patient. This involves acquisition and analysis of medical image data representing the body part of the patient which is to be treated and manual determination of the directions and doses to be applied for irradiating the patient with treatment radiation.

However, such an approach is cumbersome and prone to involve errors. Furthermore, such known manual approaches do not consider the probability for occurrence of tumour tissue in body regions which are not represented by the medical image data and/or have not been identified by the user.

SUMMARY

A problem to be solved by the invention therefore is to provide a more reliable method of determining a radiotherapy treatment plan which in particular supports radiotherapy treatment of unidentified treatment targets (such as unidentified tumour tissue).

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The method in accordance with the invention is in particular a data processing method. The data processing method is preferably performed using technical means, in particular a computer. The data processing method is in particular executed by or on the computer. Preferably, the inventive method is at least partly executed by a computer. That is, all steps or just some of the steps (i.e. less than a total number of steps) of the inventive method may be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information". In particular, "XY data" may be said to comprise (in particular consist of) "XY information". Where in the framework of this disclosure it is said that information describes an entity, the respective information in particular represents that entity. Where it is said that data processing is carried out on "XY data", it is to be understood that this data processing is carried out in particular on the corresponding "XY information".

In accordance with the invention, preferably a data processing method of determining a radiotherapy treatment plan for radiotherapy treatment of an anatomical body part of a patient's body is provided. In the context of this disclosure, radiotherapy is understood to comprise any kind of therapy which is effected by irradiating an anatomical body part of a patient's body with at least one beam of ionizing radiation. Such radiation is also termed treatment radiation (the beam is therefore also called treatment beam) and can be embodied by for example x-rays, ionizing radiation emitted from radioactive elements and/or ionizing radiation emitted from a particle accelerator. A radiotherapy treatment plan is in particular a data set comprising information about the direction of at least one treatment beam in particular relative to the anatomical body part which is to be treated. The data set preferably furthermore comprises information about the energy of treatment beams to be used (and/or about a radiation dose to be applied to the anatomical body part, which is also called treatment dose) and preferably about a time sequence of changes in the position of an arrangement of treatment beams relative to in particular the anatomical body part or the positional arrangement of the arrangement of treatment beams.

A treatment body part can be treated by one or more treatment beams issued from one or more directions at one or more times. Thus the treatment by means of the at least one treatment beam follows a spatial pattern and a time pattern. To cover the spatial and time features of the treatment by means of the at least one treatment beam, the term "beam arrangement" is used which is defined to be a synonym for "arrangement of treatment beams". The beam arrangement is an arrangement of at least one treatment beam.

The beam positions describe the positions of the treatment beams of the beam arrangement. The arrangement of beam positions is called positional arrangement. A beam position is preferably defined by the beam direction and additional information which allows to assign a specific location in in particular a three-dimensional space to the treatment beam, for example information about the coordinates in a defined coordinate system. The specific location is one point on preferably a straight line. This line is called "beam line" and runs in the beam direction and for instance runs along the central axis of the treatment beam. The defined coordinate system is preferably defined relative to the treatment device or relative to at least part of the patient's body. The positional arrangement comprises (in particular consists of) at least one beam position, in particular a discrete set of beam positions (e.g. two or more different beam positions) or a continuous multiplicity (manifold) of beam positions.

During treatment, one or more treatment beams in particular adopts the treatment beam positions defined by the positional arrangement simultaneously or sequentially (the latter in particular in case there is just one beam source to emit a treatment beam). If there are several beam sources, at least a sub-set of all beam positions can also be adopted simultaneously by treatment beams during the treatment. In particular one or more sub-sets of the treatment beams can adopt the beam positions of the arrangement in accordance with a pre-defined sequence. A sub set of treatment beams comprises one or more treatment beams. The full set of treatment beams which comprise one or more treatment beams and which adopts all beam positions defined by the positional arrangement is the beam arrangement.

The present invention relates to the field of controlling a treatment beam. The treatment beam treats body parts which are to be treated, which are referred to in the following as "treatment body parts". These body parts are in particular parts of a patient's body, i.e. anatomical body parts.

The present invention relates to the field of medicine and in particular to the use of beams, in particular radiation beams, to treat parts of a patient's body, which are also called treatment beams. A treatment beam treats body parts which are to be treated, which are referred to in the following as "treatment body parts". These body parts are in particular parts of a patient's body, i.e. anatomical body parts. Ionising radiation is in particular used for the purpose of treatment. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation are X-rays, high-energy particles (high-energy particle beams) and/or ionizing radiation emitted from a radioactive element. The treatment radiation, in particular the treatment beam, is in particular used in radiation therapy or radiotherapy, in particular in the field of oncology. For treating in particular cancer, parts of the body comprising a pathologic structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

The treatment body part can be any part of the patient's anatomical (i.e. real) body. The treatment body part in particular is a body part which comprises pathologic changes of its anatomical structure. For example, the treatment body part is a prostrate comprising tumour tissue or a brain comprising a brain tumour.

Preferably, treatment target position data comprising treatment target position information is acquired. The treatment target position information describes in particular the position of a treatment target in the treatment body part. The treatment target is to be treated by radiotherapy, i.e. by irradiation with treatment radiation. The treatment target is an anatomical treatment target, i.e. it is real and present in the patient's body. Preferably, the treatment target position data is acquired based on (in particular from) medical image data comprising medical image information which describes the (in particular, displays) treatment target. Such medical image data has preferably been generated in particular outside of the inventive method, i.e. before execution of the inventive method ensues. The medical image data is generated in particular based on the data gathered from a magnetic resonance tomography or an x-ray-based computed tomography of the treatment body part. For example, the treatment target represents tumour tissue which has been determined in the medical image information either by visual recognition or an automatic process such as image segmentation which is sensitive to different types of tissue (i.e. healthy tissue and pathologic tissue). In the context of this disclosure, a treatment target thus is to be understood as an anatomical region in which the presence of pathologic changes (in particular of tumour tissue) has been verified. The position of the treatment target is defined in particular relative to the anatomical structures in the patient's body. Advantageously, the position of the treatment target is defined in a reference system (in particular, a coordinate system) in which the radiotherapy treatment is planned. Such a coordinate system is also called a treatment coordinate system. A treatment coordinate system can be centered in the patient, i.e. rest relative to the patient's body, or in the radiotherapy system, i.e. rest relative to a component of the radiotherapy system which is used for effecting the radio therapy.

Preferably, statistic model target region position data is acquired which comprises statistic model target region position information. The statistic model target region position information describes in particular the position of a model target region in a model body part which corresponds to the treatment body part. The statistic treatment position data is generated in particular outside of the inventive method (i.e. before execution of the invention method ensues) and is preferably acquired based on (in particular from) model target position data comprising model target position information. The model target position information describes in particular the positions of model treatment targets in a plurality of human bodies which display a medical condition corresponding to the medical condition to be treated, i.e. corresponding to the medical condition of the specific patient for which the radiotherapy treatment plan is determined by execution of the inventive method. For example, model target position data is gathered from a plurality of human bodies in particular by determining the position of a tumour tissue (more particularly, of metastases or tumour foci) in each one of the plurality of human bodies which suffer from a corresponding (in particular the same) tumour disease as the specific patient. Each one of the plurality of model bodies advantageously differs from the current patient's body, i.e. none of the model bodies is identical to the patient's body. Whether the medical condition, in particular the tumour disease, of the plurality of human bodies (in the framework of this disclosure also called "model bodies") and the specific patient correspond to each other, in particular are the same, can be determined by comparing the pathologic parameters of the patient and each one of the model bodies. The pathologic parameters are advantageously defined by a medical classification such as a classification of patients according to in particular the position of pathologic changes in the anatomical structure in each one of the plurality of human bodies, in particular the TNM classification or the International Classification of Diseases (ICD). For example the TNM system for classification of malignant tumours is applied and it is evaluated whether each one of the plurality of human bodies and the specific patient are assigned the same TNM classification. The statistic treatment region position data is then preferably generated based on (in particular by) determining spatial target region cluster data comprising spatial target region cluster information. The spatial target region cluster information describes in particular a spatial clustering of the model treatment targets in the plurality of human bodies. A spatial clustering in the context of this disclosure is understood to describe in particular a geometric concentration of the model treatment target in at least one specific anatomic region of all of the plurality of human bodies used for generating the statistic treatment position data. For example, such a cluster describes a statistical distribution of the pathologic changes of anatomic structures in the plurality of human bodies, in particular a delimited volume in a combination (e.g. an atlas) generated from the model bodies in which an increased occurrence of pathologic changes compared to other anatomical structures has been determined, in particular is present.

Preferably, the spatial target region cluster data is determined based on combining sets of medical image data comprising the model target region position information for each individual one of the plurality of model bodies. For example, medical image data is acquired for each one of the plurality of model bodies and in particular segmented in order to determine the position of pathologic changes, in particular of tumour tissue, in each one of the model bodies. The sets of medical image data are combined by for example image fusion (in particular, elastic fusion) of the sets which results in essentially overlaying the sets of medical image data. The combined sets of medical image data are then preferably analyzed (for example, by image segmentation) for regions which display a comparably high spatial concentration of model treatment targets. Such regions are then determined to represent the spatial clusters. In particular, this procedure results in generating a generic, in particular statistic, model of a patient's body, in particular of a model body part corresponding to the treatment body part which comprises a statistic distribution of the mentioned pathologic changes. Such a model of a patient's body is also termed an atlas in the framework of this disclosure.

The verb "to correspond" and the adjective "corresponding" in the framework of this disclosure in particular means that the "corresponding" features are anatomically the same, in particular that they represent the same body part which is present in the plurality of different human bodies and/or which consists of the same material and/or which is located at least approximately at the same location relative to other anatomical structures and/or which have a similar geometry (i.e. size and/or shape) in a plurality of (real) different human bodies.

An atlas typically consists of a plurality of generic models of objects, wherein the generic models of the objects together form a complex structure. The atlas of a femur, for example, can comprise the head, the neck, the body, the greater trochanter, the lesser trochanter and the lower extremity as objects which make up the complete structure. The atlas of a brain, for example, can comprise the telencephalon, the cerebellum, the diencephalon, the pons, the mesencephalon and the medulla as the objects which make up the complex structure. One application of such an atlas is in the segmentation of medical images, wherein the atlas is matched to medical image data, and the image data are compared with the matched atlas in order to assign a point (a pixel or voxel) of the image data to an object of the matched atlas, thereby segmenting the image data into objects.

Preferably, irradiation region position data is determined based on the treatment target data and the statistic model target region position data (in particular based on the irradiation region position data). The irradiation region position data comprises irradiation region position information which describes (in particular represents) the position of an irradiation region to be treated by irradiation with treatment radiation. The irradiation region is located in particular in the treatment body part. As described above, the statistic model target region position data is generated based on model target information acquired for a plurality of human bodies which have the same pathologic parameter as the specific patient to be treated by application of the inventive method. For example, the model target position data is acquired only from human bodies which have the position of at least some pathologic changes such as tumour tissue at a corresponding, in particular the same, position as the specific patient. This corresponding position in particular is the position of the treatment target described by the treatment target position information.

The irradiation region is in particular a region which is to be irradiated with treatment radiation and corresponds in particular to a spatial cluster described by the spatial target region cluster information. In particular, the position of the at least one spatial cluster described by the spatial target region cluster information is mapped to the treatment body part of the specific patient for example by fusion (in particular, elastic fusion) of treatment body part position data comprising treatment body part position information describing the position of the treatment body part which is acquired based on (in particular from) preferably medical image data describing the treatment body part and the statistic model target region position data (more particularly, the spatial target region cluster data). In particular, the statistic treatment region position data (the spatial target region cluster data) is mapped onto (fused to) the treatment body part position data.

In this application, the term "image morphing" is also used as an alternative to the term "image fusion", but with the same meaning. Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $1/10$ or $1/100$ or $1/1000$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (in particular a first and a second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity. A measure of similarity can in particular be determined on the basis of a determined correlation between the first and second data set.

The aforementioned fusion algorithm in particular determines an elastic fusion transformation which is preferably used to determine a degree of similarity (more particularly, a "measure of similarity") between the static medical image information and the patient model information. To this end, the deviation of the elastic fusion transformation and an identity transformation is determined. The degree of deviations can for instance be calculated by determining the difference between the determinant of the elastic fusion transformation and the identity transformation. The higher the deviation is, the less the similarity. Thus, a measure of similarity can in particular be determined on the basis of a determined correlation between the static medical image information and the patient model information.

The target region can be located inside or outside the irradiation region. In particular the position of the irradiation region does not necessarily comprise the position of the target region. More particularly, the disclosed method relies on determining the occurrence, in particular a measure of probability for the occurrence, of additional treatment targets based on the treatment target position data. The irradiation region may therefore in fact comprise additional treatment targets or be selected for irradiation merely as a precautionary measure based on clinical statistics for the spatial-temporal development of the specific pathologic changes, in particular for creation of further tumour tissue, in particular in the form of metastases. Therefore, the irradiation region position information preferably comprises position probability information which describes a position probability for the irradiation region having the determined position. That is, the determined position of the irradiation region corresponds to the position of the at least one spatial cluster described by the spatial target region cluster information, wherein the cluster in turn describes a high spatial concentration (i.e. a high density) of pathologic changes, in particular a spatial accumulation of pathologic changes. Since the positions of such pathologic changes may vary among the plurality of model bodies on the basis of which the statistic treatment position data is generated, a geometric region may be drawn in particular as a three-dimensional outline of the positions of these pathologic changes for all of the model bodies. Such a region is in the context of this disclosure called a model target region. In summary, the irradiation region corresponds to a mapping of the model target region from the model body part of each model body to the treatment body part. The irradiation region position information therefore also comprises statistic information about the occurrence of further pathologic changes (in particular, metastases or tumour foci) which in particular describes a measure for the occurrence probability of further pathologic changes in the treatment body part based on clinical data. Such occurrence probability is described by the position probability information which is determined in particular based on the spatial density (in particular spatial concentration) of the further pathologic changes in the description of the treatment body part. Regions displaying a comparatively high position probability (a high spatial density of pathologic changes) are then determined as irradiation regions.

Preferably, irradiation dose data is determined based on the irradiation position data. The irradiation dose data comprises irradiation dose information which describes in particular an irradiation dose to be applied to the irradiation region. The irradiation dose in particular is a treatment dose which in general has to exceed a predetermined threshold value which depends on clinical parameters in order to achieve a treatment effect in any pathologic changes. Therefore, the irradiation dose data preferably either indicates that the irradiation dose is zero, i.e. the irradiation region is not to be irradiated, or that it has a value which is at least the predetermined threshold value for achieving a treatment effect. Among the determined irradiation regions, also only such irradiation regions may be selected as a basis for determining the irradiation dose data for which the position probability exceeds a predetermined threshold, in particular in which the spatial density of potential further target regions exceeds a predetermined value. In this case, only irradiation regions for which the position probability exceeds such a predetermined value are to be irradiated with treatment radiation.

According to a specific embodiment of the invention, preferably verification image data is acquired which comprises verification image information. The verification image information describes in particular a medical image of the irradiation region. In particular, the verification image data is acquired based on the irradiation region position data in order to verify the irradiation region position information, in particular the presence of pathologic changes such as tumour tissue (in particular, metastases) in the treatment body part at the position of the irradiation region, in particular inside the irradiation region. In particular, it is determined whether the verification image information describes a treatment target, in particular at least one additional treatment target which is additional to the treatment target described by the treatment target position information. The irradiation region position information and the verification image information can be compared in particular by application of a fusion algorithm for fusing the two data sets and then determining the differences between them. Based on the comparison, it is then preferably determined whether the irradiation region is to be irradiated. In particular, the irradiation region is to be irradiated with the treatment radiation only if the result of the comparison indicates that the verification image information describes a treatment target, in particular if the result of the comparison indicates that the irradiation region comprises at least one treatment target.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The invention is also directed to a radiotherapy system comprising the aforementioned computer for executing the data processing steps of the inventive method, in particular for processing the static medical image data and the patient model data and for determining data wherever desired when executing the inventive method. The radiotherapy system preferably comprises an irradiation unit for emitting treatment radiation for radiotherapy of in particular tumour tissue. The irradiation unit is controlled by the computer of the radiotherapy system and is preferably moveable, in particular moveable relative to a treatment position of the patient's body, i.e. a position which the patient's body has during radiotherapy. To this end, preferably at least one moving unit is operatively coupled to the irradiation unit and a bed on which the patient is placed for treatment, the at least one moving unit being preferably also controlled by the computer of the radiotherapy system. The at least one moving unit in particular comprises an electric motor and the gear system for moving the irradiation unit and the patient bed. Furthermore, the computer is also configured to control activation of the irradiation unit, i.e. to control the operating parameters of the irradiation unit, in particular the energy of the treatment radiation and the point in time at which to emit treatment radiation.

The inventive method preferably also comprises a step of using the aforementioned data processing method for determining the control parameters of the radiotherapy system for irradiating the patient's body. This is in particular done by determining radiotherapy plan data comprising radiotherapy plan information. The radiotherapy plan information describes in particular at least one control parameter of the radiotherapy system, in particular at least one of an irradiation dose, a time of irradiation and the irradiation direction for irradiation of the patient's body, in particular of the anatomical body part. The radiotherapy plan data is preferably determined based on the irradiation region position data, in particular based on information about the anatomical body part in at least one of the second and third anatomical movement states. The radiotherapy plan data is then preferably used to pre-configure the radiotherapy system before the radiotherapy treatment actually starts. For example, the radiotherapy plan data is read by the computer of the radiotherapy system and the computer generates instructions to be executed by the radiotherapy system based on the radiotherapy plan data. Execution of the instructions and corresponding operation of the radiotherapy system can then be activated by an operator at the desired point in time.

The data processing method of determining a radiotherapy treatment plan is preferably executed before or during radiotherapy treatment. That means, the data processing method is preferably executed before the first application of treatment radiation or between the first and the last application of treatment radiation to the patient's body (in particular, the first and the last application in one treatment session).

The disclosed method, in particular any method step associated with or directed to acquiring the medical image information or the medical image selection information, does not involve an invasive step which would represent the substantial physical interference with the human or animal body requiring professional medical expertise to be carried out and entailing a substantial health risk even when carried out with the required professional care and expertise. Furthermore, no part of the inventive method involves a step of treating a human or animal body using surgery or therapy. Rather, the invention is said to also relate to a method of planning a radiotherapy treatment or controlling a radiotherapy system which comprises the disclosed method of determining a treatment plan rather than calling it a method of treating the patient's body by radiotherapy. Furthermore the disclosed method of determining a treatment plan is executed advantageously (entirely) before treatment by radiotherapy is conducted.

BRIEF DESCRIPTION OF THE DRAWINGS

In the following, the invention shall be described with reference to the figures which are to be understood as an exemplary explanation of the invention and shall not be construed to limit the invention to only those features which are shown in the figures.

DETAILED DESCRIPTION

Figure 1:
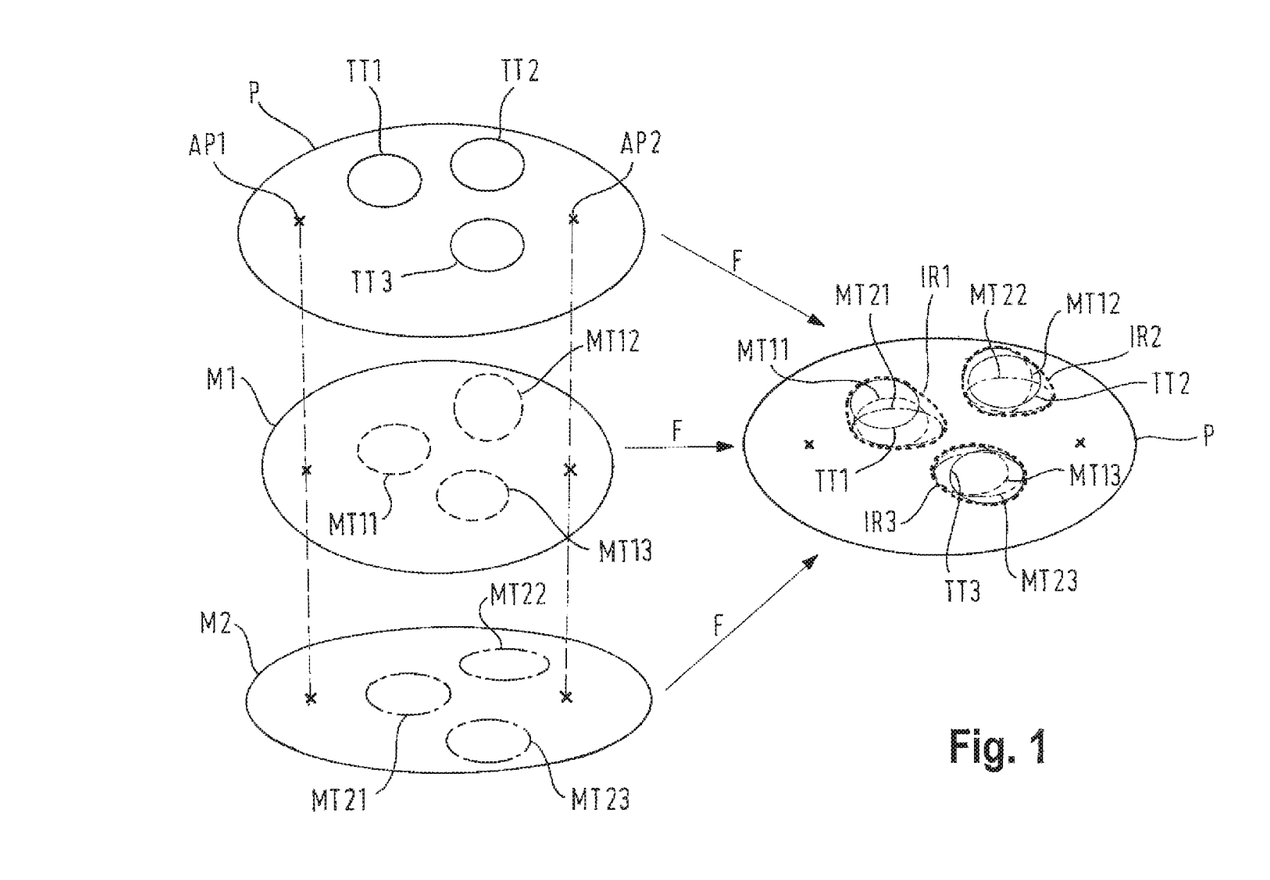
FIG. 1 is a schematic representation of how to combine the treatment target position data and the statistic model target region position data.

FIG. 1 is a schematic view of how to combine treatment target position information gathered for the treatment body part P of a specific patient with model target position information gathered for model body parts M1, M2 of two different model bodies. For example, medical image data is generated from a magnetic resonance tomography (MRT) or positron emission tomography (PET) or from projecting and manually tracing a thin cut biopsy sample of an anatomical body part P of the patient 7 which describes the positions of treatment targets TT1, TT2, TT3. From a plurality of model bodies, model target position data is acquired (for example also by applying a medical imaging method to the model bodies) which indicates the positions of model treatment targets MT11, MT12, MT13 and MT21, MT22, MT23, respectively. In each of the data sets for P, M1 and M2, anchor points AP1, AP2 are defined. The anchor points AP1, AP2 are preferably defined as representing corresponding anatomical structures in each one of the anatomical body part P of the patient 7 and the model body parts M1 and M2 of the model bodies. The treatment target position information for the treatment body part of the patient 7 and the statistic model target region position information for the model body parts M1 and M2 are overlaid onto one another by applying a fusion transformation F, wherein the anchor points are AP1, AP2 serve as a positional reference in order to transform the positions described by the treatment target position information and the statistic model target regional position information (in particular the model target position data) into a common reference system. Alternatively, the statistic model target region position information may be generated by first overlaying the model target position information of the model targets MT12, . . . , MT13 with the model target position information for the model targets MT21, . . . , MT23 in order to generate a single model data set which represents in particular an anatomical atlas for the model body parts M1, M2 which is then fused with the treatment target position information for the treatment body part P.

The result of the fusion transformation then is a data set for the treatment body part P comprising irradiation region position data (and irradiation region position information) for the irradiation region IR1, IR2, IR3. The irradiation regions IR1, . . . , IR3 in this case comprise each of the target regions TT1, . . . , TT3 and are represented by an outline (dotted in FIG. 1) which contains each of the treatment targets TT1, . . . , TT3 and the respectively closest model target MT11, . . . , MT13, MT21, . . . , MT23. The irradiation regions IR1, . . . , IR3 represent regions in the treatment body part of the patient P which are to be irradiated with treatment radiation at a higher dose than the tissue surrounding the irradiation regions IR1, . . . , IR3. The irradiation regions are therefore also termed "boost regions" in which the beam energy and/or the treatment dose is raised significantly compared to surrounding tissue. In particular, the surrounding is not irradiated at all, i.e. receives a zero dose.

Figure 2:
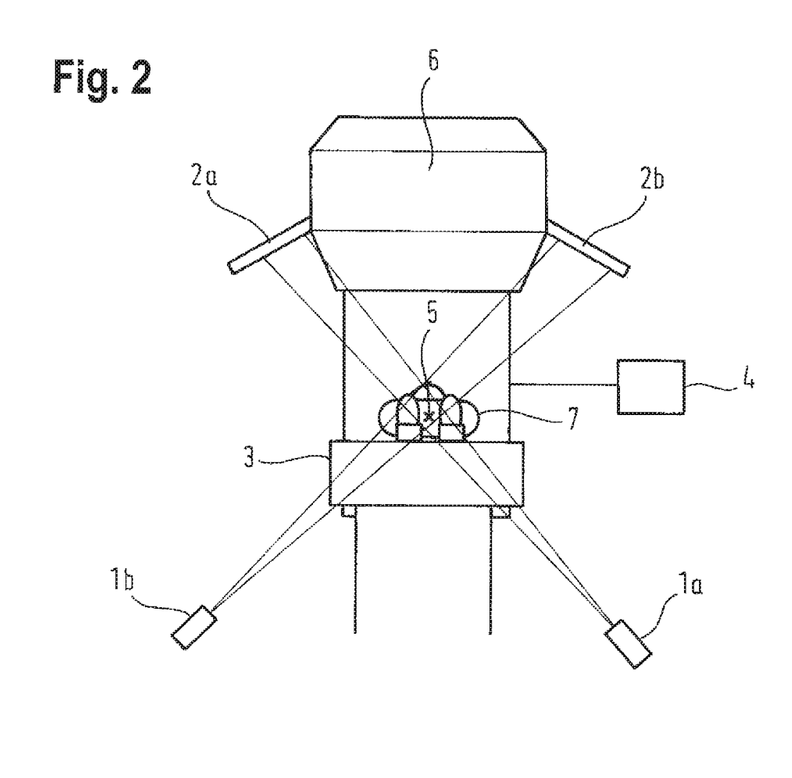
FIG. 2 is a depiction of a radiotherapy system with a patient placed on a treatment bed.

FIG. 2 gives an impression of a radiotherapy system comprising an irradiation unit embodied by a linear accelerator 6, a treatment table 3 on which a patient 7 is placed for treatment and a computer (4) for controlling operation of the linear accelerator (in particular for controlling the beam energy) and for controlling movement of both the linear accelerator 6 and the treatment table 3 in order to place the treatment body part 5 of the patient 7 in a desired position relative to the treatment beam emitted by the linear accelerator 6. Correct positioning of the treatment body part 5 can be verified by for example taking medical image data with x-ray tubes 1a, 1b, the transmission signals of the x-rays being detected by x-ray detectors 2a, 2b which can be embodied by for example semiconductor-based detectors which are sensitive to x-rays.

Figure 3:
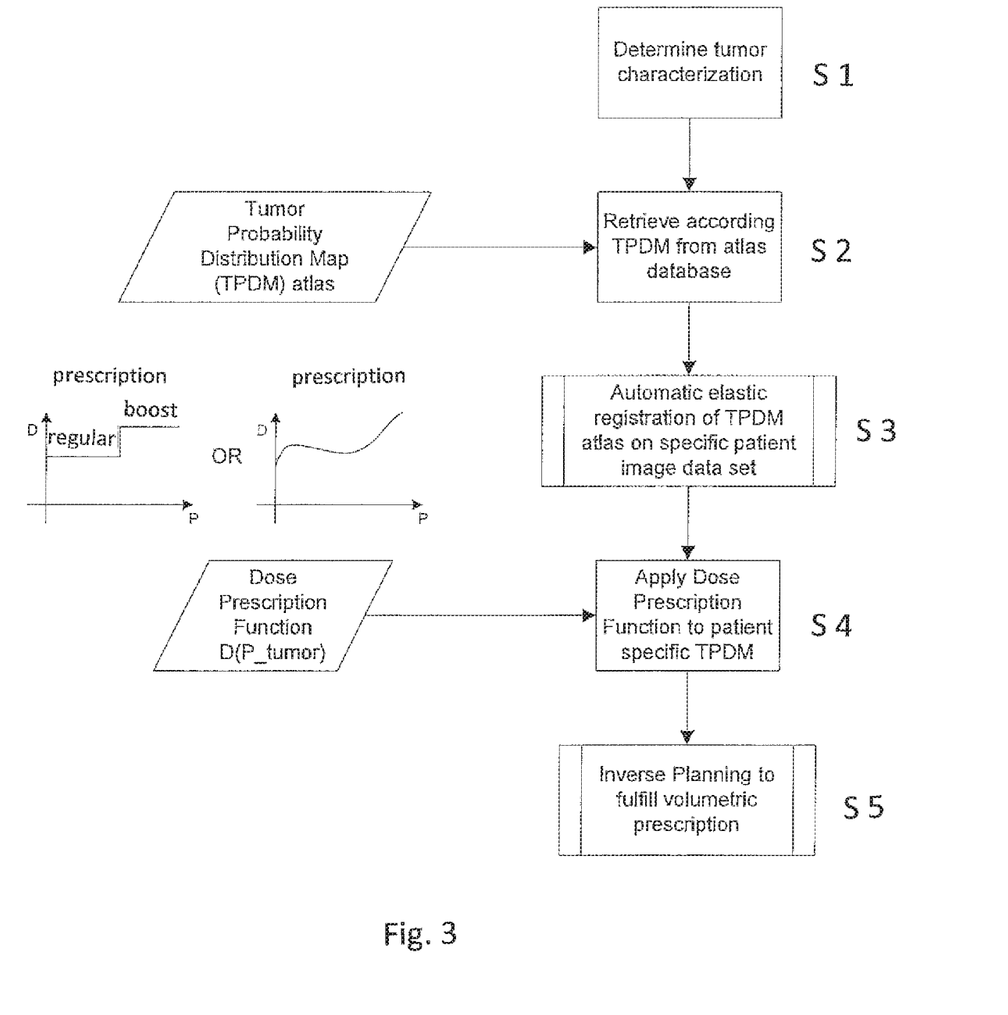
FIG. 3 is a flow diagram for an exemplary embodiment of the inventive method.

FIG. 3 is a flow diagram for an exemplary embodiment of the invention which describes a flow of the inventive method. In step S1, the treatment target position data is acquired in order to determine a categorization of the tumour. In step S2, a tumour probability distribution map TPDM is retrieved from an atlas database on the basis of the tumour characterization determined in step S1. The data describing the TPDM corresponds to the statistic model target region position data. The method continues to step S3 which comprises an automatic elastic registration of the TPDM atlas to an image data set comprising medical image information of the treatment body part P of the specific patient. The elastic registration is effected in particular by an elastic fusion algorithm. Depending on the characterization of the tumour determined in step S1, a dose prescription function D(P_tumor) is then determined in step S4 from a database and applied to the patient-specific TPDM, i.e. to the result of the elastic registration performed in step S3. D(P_tumor) represents the irradiation dose D for a specific position in the treatment body part P as a function of the position probability P_tumor for tumour tissue being present at that position and is for example a continuous function or a step function. In the case of the step function, a specific, "regular" dose is predetermined (in particular has a value of zero) for irradiation of for example the whole treatment body part P and a "boost" value which is to be applied to the irradiation regions IR1, . . . , IR3 (boost regions). In the D-P-diagrams of FIG. 3, the quantity P is equal to P_tumor and shall not be confused with the treatment body part P. As a result of step S4, a treatment dose distribution to be applied to the treatment body part P is received.

In order to determine further components of the radiotherapy treatment plan, the method then continues to step S5 for inverse planning of the radio therapy treatment to fulfil the volumetric prescription. In particular, step S5 comprises determining the required beam energies and beam directions in order to generate the treatment dose distribution received in step S4. To this end, step S5 considers the control parameters of the radiotherapy system as well as medical boundary conditions, for example the positions of organs at risk, irradiation of which is to be avoided as far as possible.

What is claimed is:

1. A method of determining a radiotherapy treatment plan for radiotherapy treatment of a treatment body part of a patient's body, the method being executed by a computer and comprising the following steps:
   a) acquiring treatment body part position data indicating a position of the treatment body part and treatment target position data comprising treatment target position information describing the position of a treatment target to be treated by radiotherapy in the treatment body part;
   b) acquiring statistic model target region position data comprising statistic model target region position information describing the position of a model target region in a model body part corresponding to the treatment body part,
      wherein the statistic model target region position data has been generated based on model target position data comprising model target position information describing the positions of model treatment targets in a plurality of model bodies which display a medical condition corresponding to the medical condition to be treated, wherein the statistic model target region position data comprises spatial target region cluster data comprising spatial target region cluster information describing at least one spatial cluster that defines a geometric concentration of the model treatment targets in at least one specific anatomic region in all of the plurality of model bodies, and
wherein the spatial target region cluster data is determined based on combining sets of medical image data comprising the model target region position information for each individual one of the plurality of model bodies;
c) determining, by mapping the statistic model target region position data to the treatment body part position data, irradiation region position data comprising irradiation region position information describing the position of an irradiation region to be treated by irradiation with treatment radiation in the treatment body part; and
d) outputting the irradiation region position data to a radiotherapy system, including an irradiation unit configured to emit treatment radiation, for positioning of the irradiation unit according to the irradiation region position data.

2. The method according to claim 1, wherein the treatment target position data is generated based on medical image data comprising medical image information describing the treatment target, the medical image data having been generated in particular based on a magnetic resonance tomography or a computed tomography of the treatment body part.

3. The method according to claim 1, wherein the irradiation region position information is determined based on position probability information describing a position probability for the irradiation region having the determined position.

4. The method according to claim 3, comprising a step of determining, based on the irradiation region position data, irradiation dose data, the irradiation dose data comprising irradiation dose information describing an irradiation dose to be applied to the irradiation region.

5. The method according to claim 4, wherein the irradiation region position data is determined by fusing the statistic model target region position data with the treatment body part position data describing the position of the treatment body part.

6. The method according to claim 3, wherein it is determined that the irradiation region is to be irradiated with treatment radiation only if the position probability exceeds a predetermined value.

7. The method according to claim 1, comprising a step of acquiring verification image data comprising verification image information describing a medical image of the irradiation region, wherein the irradiation region position information is verified by comparing it to the verification image information, in particular by determining whether the verification image information describes a treatment target.

8. The method according to claim 7, wherein it is determined that the irradiation region is to be irradiated with the treatment radiation if the result of the comparison indicates that the verification image information describes a treatment target, in particular if the result of the comparison indicates that the irradiation region comprises at least one treatment target.

9. The method according to claim 1, wherein the treatment target is located inside or outside the irradiation region.

10. The method according to claim 1, wherein the treatment target comprises tumour tissue.

11. A non-transitory computer-readable storage medium having stored thereon computer-executable instructions that, when executed, configure a processor to:
a) acquire treatment body part position data indicating a position of a treatment body part and treatment target position data comprising treatment target position information describing the position of a treatment target to be treated by radiotherapy in the treatment body part;
b) acquire statistic model target region position data comprising statistic model target region position information describing the position of a model target region in a model body part corresponding to the treatment body part,
wherein the statistic model target region position data has been generated based on model target position data comprising model target position information describing the positions of model treatment targets in a plurality of model bodies which display a medical condition corresponding to the medical condition to be treated,
wherein the statistic model target region position data comprises spatial target region cluster data comprising spatial target region cluster information describing at least one spatial cluster that defines a geometric concentration of the model treatment targets in at least one specific anatomic region in all of the plurality of model bodies, and
wherein the spatial target region cluster data is determined based on combining sets of medical image data comprising the model target region position information for each individual one of the plurality of model bodies;
c) determine, by mapping the statistic model target region position data to the treatment body part position data, irradiation region position data comprising irradiation region position information describing the position of an irradiation region to be treated by irradiation with treatment radiation in the treatment body part; and
d) output the irradiation region position data to a radiotherapy system, including an irradiation unit configured to emit treatment radiation, for positioning of the irradiation unit according to the irradiation region position data.

12. A system for determining a radiotherapy treatment plan for radiotherapy treatment of a treatment body part of a patient's body, the system comprising:
an electronic data storage device; and
a processor operably coupled to the electronic data storage device and configured to:
a) acquire treatment body part position data indicating a position of the treatment body part and treatment target position data comprising treatment target position information describing the position of a treatment target to be treated by radiotherapy in the treatment body part;
b) acquire statistic model target region position data comprising statistic model target region position information describing the position of a model target region in a model body part corresponding to the treatment body part,
wherein the statistic model target region position data has been generated based on model target position data comprising model target position information describing the positions of model treatment targets in a plurality of model bodies which display a medical condition corresponding to the medical condition to be treated, wherein the statistic model target region position data comprises spatial target region cluster data comprising spatial target region cluster information describing at least one spatial cluster that defines a geometric concentration of the model treatment targets in at least one specific anatomic region in all of the plurality of model bodies, and wherein the spatial target region cluster data is determined based on combining sets of medical image data comprising the model target region position information for each individual one of the plurality of model bodies;

c) determine, by mapping the statistic model target region position data to the treatment body part position data, irradiation region position data comprising irradiation region position information describing the position of an irradiation region to be treated by irradiation with treatment radiation in the treatment body part; and d) output the irradiation region position data to a radiotherapy system, including an irradiation unit configured to emit treatment radiation, for positioning of the irradiation unit according to the irradiation region position data.

* * * * *